United States Patent [19]

Hietala et al.

[11] Patent Number: 5,372,982
[45] Date of Patent: Dec. 13, 1994

[54] CATALYST FOR METATHETIC REACTIONS OF OLEFINS

[75] Inventors: Jukka Hietala; Pekka Knuuttila, both of Porvoo; Arla Kytökivi, Espoo, all of Finland

[73] Assignee: Neste Oy, Espoo, Finland

[21] Appl. No.: 913,723

[22] Filed: Jul. 16, 1992

[30] Foreign Application Priority Data

Jul. 16, 1991 [FI] Finland .................................. 913439

[51] Int. Cl.[5] .................... B01J 27/138; B01J 27/135; B01J 21/08
[52] U.S. Cl. .................... 502/226; 502/228; 502/251; 502/254
[58] Field of Search ................. 502/226, 228, 251, 254

[56] References Cited

U.S. PATENT DOCUMENTS

| | | | |
|---|---|---|---|
| 3,413,367 | 11/1968 | Kopsch .................. | 502/228 |
| 4,194,992 | 3/1980 | Corbellini et al. ......... | 502/113 |
| 4,203,866 | 5/1980 | Corbellini et al. ......... | 502/113 |
| 4,217,245 | 8/1980 | Corbellini et al. ......... | 502/113 |
| 4,446,289 | 5/1984 | Carbonaro et al. ........ | 502/107 |
| 5,071,812 | 12/1991 | Kelsey .................. | 502/164 |

FOREIGN PATENT DOCUMENTS 703628  2/1954  United Kingdom .
989085  4/1965  United Kingdom .

Primary Examiner—Helen M. S. Sneed
Assistant Examiner—E. D. Irzinski
Attorney, Agent, or Firm—Birch, Stewart, Kolasch & Birch

[57] ABSTRACT

The present invention concerns a heterogeneous catalyst particularly suited to the metathetic reactions of olefins in liquid or gas phase. Such a catalyst generally includes catalytically active species of tungsten on an inorganic support. The catalyst in accordance with the invention is prepared by vaporizing a precursor of tungsten, such as tungsten oxychloride or hexachloride and then routing the vapor of the tungsten-containing reagent into a reaction space, where the vapor is brought to interaction with the support material at approximately 160° to 500° C. The vapor pressure of the tungsten-containing reagent is kept sufficiently high, and the duration of interaction with the support sufficiently long, to keep the amount of the reagent at least equal to the number of available bonding sites of the support, whereby the bonding of the tungsten-containing reagent to the support surface is determined by the surface properties of the support. The catalyst can be post-treated after its preparation to modify its catalytic activity. The specific activity of the catalytic metal species of the catalyst according to the invention is high.

12 Claims, 2 Drawing Sheets

Activity of catalyst as a function of the W species content

Activity of catalyst as a function of the W species content

Effect of pretreatment and bonding temperatures on the tungsten content of the catalyst

CATALYST FOR METATHETIC REACTIONS OF OLEFINS

BACKGROUND OF THE INVENTION

1. Field of the Invention

The present invention relates to a heterogenous catalyst particularly suited to the metathetic reactions of olefins.

2. Description of the Related Art

Such a heterogeneous catalyst conventionally comprises a support, consisting of an inorganic oxide or a mixture of inorganic oxides, and a tungsten compound bonded to the surface of the support.

The terms metathesis, disproportionation or dismutation are used to refer to a catalytic reaction in which asymmetric olefin molecules are converted to new olefins having a hydrocarbon chain longer or shorter than that of the precursor olefin. Thus, propene for instance reacts in the presence of said catalysts to form ethene and butene. Further, two different kinds of olefin molecules can react in a metathetic manner exemplified by the reaction of ethene and 2-butene forming propene. Other areas of application of metathetic catalysts are, e.g., disproportionation by ring opening, and the utilization of olefins having a carbon number of less than 10 and more than 20 that result from the oligomerization of ethene by way of first isomerizing them into i-olefins and then allowing them to react mutually in the presence of a metathetic catalyst. Another utilization method of said olefins is to allow them to react after isomerization with ethene in the presence of a metathetic catalyst to produce odd-carbon α-olefins, from which fractions suitable for raw materials for making lubricants can be separated by fractionation.

Catalysts for metathetic reactions are today prepared by conventional methods, which include the impregnation of a support with a precursor of the active metal species from a solution of the metal salt, the co-precipitation of the metal salt and the support material and the coextrusion of the support and the precursor of the catalyst. Generally, an essential step in the preparation of the catalyst also comprises the activation of the catalyst by heating at an elevated temperature in the presence of air or an inert gas. Typical catalysts of this kind include the oxides of Re, W and Mo on a silica gel or alumina support, or on a mixture-type support.

The above-described preparation methods of heterogeneous catalysts are poorly suited to control the bonding of the active catalyst materials onto the support material surface (that is, the control of the dispersion of the catalyst).

The surface of the powdered particles in support materials used in heterogeneous catalysts is structurally inhomogeneous. Therefore, the methods of the conventional technology are poorly suited for a controlled bonding of a metal species or metal compound.

SUMMARY OF THE INVENTION

It is an object of the present invention to overcome the disadvantages associated with the conventional technology and to achieve a catalyst prepared by a novel method, said catalyst containing tungsten on an inorganic oxide support.

The invention is based on the concept of evaporating a precursor of tungsten, preferably tungsten oxychloride or hexachloride, advantageously at a temperature of at least 160° C. and routing the vapor into a reaction space, where the vapor is brought into interaction with the support. The support temperature is maintained above the condensation temperature of the vapor and simultaneously so high as to attain the thermal activation energy necessary for establishing the bonds between the precursor of the tungsten compound and the support material. According to the invention, the preferred operating temperature is about 160° to 500° C. Advantageously, the support material is silica gel (that is silicon dioxide) or a silica cogel of different metals. The precursor of the tungsten species is introduced in vapor phase in at least an equal amount to the bonding sites available on the support material surface.

More specifically, the catalyst in accordance with the invention is prepared by vaporizing a tungsten-containing reagent selected from the group consisting of tungsten oxychloride and tungsten hexachloride, routing the vapor of the tungsten-containing reagent into a reaction space where the vapor is reacted with the support material at about 160° to 500° C., maintaining the vapor pressure of the tungsten-containing reagent sufficiently high and the duration of interaction with said support sufficiently long so as to provide said reagent in an amount at least equal to the number of available bonding sites on said support material, and removing said tungsten-containing reagent not bonded to said support material from the reaction space in the vapor phase.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description

BRIEF DESCRIPTION OF THE DRAWINGS

The present invention will become more fully understood from the detailed description given hereinbelow and the accompanying drawings, which are given by way of illustration only and thus not limiting of the present invention, and wherein.

DETAILED DESCRIPTION OF THE INVENTION

Figure 1:
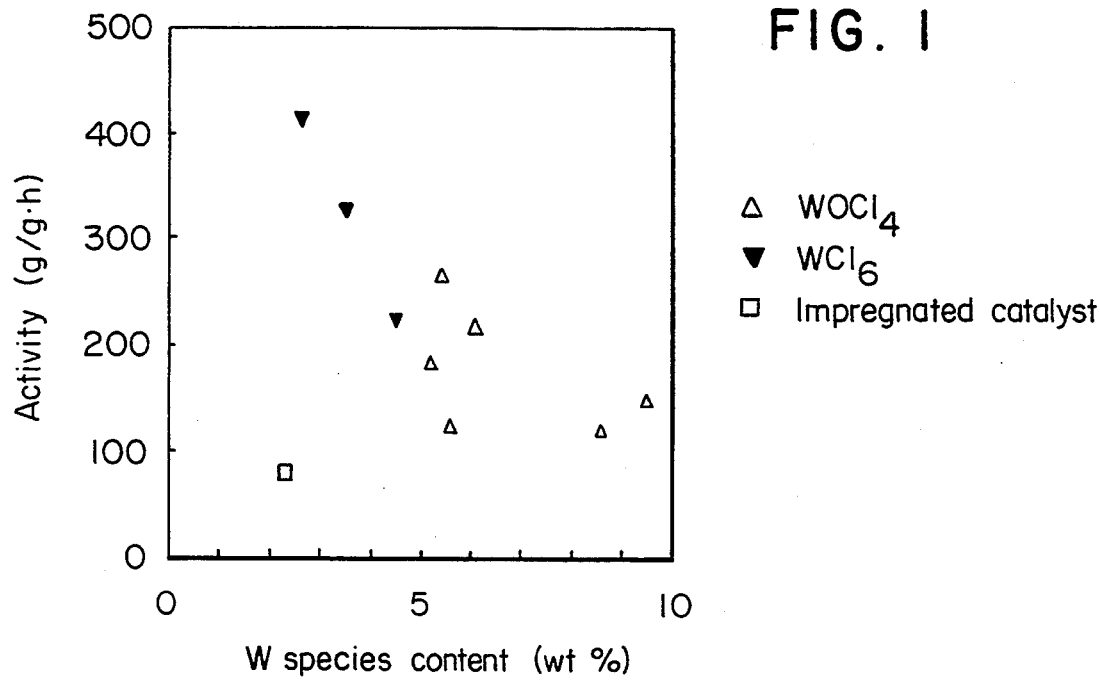
FIG. 1 is a graph showing the activity of $W/SiO_2$ catalysts prepared using different kinds of reagents in the metathetic reaction of propene, as a function of the W species content.

By way of the present invention, it is possible to attain an improved diffusion and dispersion of the metal species into the support material over that provided by conventional impregnation methods, whereby the specific activity of the metal is enhanced.

Lacking yet the full knowledge of all details related to the matter, the present inventors do not wish to be limited by any theoretical model. However, it is possible that the structural geometry of the surface-site atoms on the support surface and their electron distribution (i.e. the potential energy function of the surface) determine the bonding of the catalytically active tungsten compound to the different sites of the surface under conditions in accordance with the invention. The tungsten compound is bound by chemisorption, which takes place selectively at the surface sites.

The preparation of the $WO_3/SiO_2$ catalysts is based on the chemisorption of vaporizable reactants from vapor phase onto the support surface. The preparation process is comprised of the following phases: 1) preheating of the oxide support, 2) vaporization of the reactant and its bonding reaction to the support surface, 3) a possible posttreatment (e.g., heating and nitrogen flushing or water vapor treatment).

According to the invention, all reagents for pretreatment, metal species bonding, and posttreatment are brought into the reaction space in vapor phase, typically one component at a time. Here, the vapor pressure of the evaporated tungsten reagent containing the catalytically active material or its precursor is kept sufficiently high during the process, and the duration of interaction with the support material surface is kept sufficiently long, so as to achieve saturation or, advantageously, supersaturation with the active material or its precursor, respectively, at the bonding sites of the support material. The proportion of excess active material used in relation to the concentration necessary to achieve complete saturation of all available bonding sites on the support material surface (customarily called a monolayer coverage) is typically 1- to 100-fold, preferably 1- to 3-fold. The amount of the tungsten compound necessary for a monolayer coverage can be calculated from the area of the silica gel support determined with the help of, e.g., the BET method, and from the known molecular structure of the support.

The reaction temperature must not fall below the temperature necessary for the evaporation of the reagent; otherwise, condensation of the reagent could occur. Further, the reagent must not be allowed to condense on its way to the reaction space; therefore, its temperature must not be allowed to fall below the reaction temperature. The tungsten compound and the operating temperature must be selected so as to avoid the decomposition of the metal compound or a possible condensation of its decomposition products.

Using experimental methods, it is possible to determine a temperature range, or temperature span, in which the reaction is most advantageously carried out. As explained above, the invention is carried out at a temperature in the range from about 160° to about 500° C., preferably at about 175° to 450° C. The lower limit of the given temperature span is determined by the condensation temperature of the tungsten compound to be evaporated at the employed partial vacuum and by the activation energy necessary for establishing a desired surface bond. The upper limit is determined by the temperature at which the tungsten compound chemisorbed on the support starts to show an essential rate of desorption from the desired bonding states, that is, when the equilibrium of the chemisorption-desorption reaction has shifted toward desorption.

The reaction between the catalytically active material or its compound and the support can be carried out at ambient pressure, or alternatively, at overpressure. Advantageously, the reaction is, however, carried out in a partial vacuum. Typically, the operating pressure in the process is in the range from 0.1 to 100 mbar, preferably in the range from approximately 1 to approximately 100 mbar. Also, pre- and posttreatment steps, if any, are preferably carried out in a partial vacuum. A benefit gained from the use of a partial vacuum is that the reaction space is kept cleaner, and the diffusion rate is increased. The reaction time is not particularly critical, as long as it is sufficient to allow the evaporated reagent to interact with the bonding sites of the support. Thus, the reaction time can be selected, for instance, in the range from 0.5 to 25 hours, the reaction time typically being 1 to 10 hours for processing a 5 to 20 gram amount of the support material.

The evaporated tungsten compound can be introduced into the reaction space as such, or alternatively, by using an inert carrier gas such as nitrogen or noble gases. Advantageously, a protective gas atmosphere formed by an inert gas is used, whereby the same inert gas is used as the carrier gas for the tungsten compound vapor.

In the preparation of a catalyst according to the invention, the support can be subjected to a pretreatment at elevated temperatures prior to the actual bonding reaction. The heat treatment of the support can be applied to modify the number and character of the OH groups on the support and, thereby, the amount of bonded metal species. An elevated pretreatment temperature reduces the number of excess OH groups and diminishes side reactions catalyzed by acid sites. The heat pretreatment is carried out at, e.g., 200° to 600° C. for 1 to 40 hours, preferably for 2 to 24 hours.

The saturation level and degree, that is, the W species content, can be modified by varying such parameters as the pretreatment temperature of the support or the bonding temperature of the reactant, or by using an alternative support or reactant. The pretreatment temperature has a much more pronounced effect on the W species content than the bonding temperature, as will be evident from an example to be described below.

Chloride residues originating from the precursor of the tungsten species, which may reduce the activity of the catalyst, can be removed from the catalyst after the bonding reaction by a water vapor treatment.

Any unreacted tungsten reagent is removed from the reaction space in the vapor phase.

The catalyst is frequently subjected to a posttreatment in order to modify its activity, particularly to activate the catalyst. Typically, the tungsten compound chemisorbed onto the support surface is converted by calcining into tungstenate which by a continued feed of the compound or with the help of an auxiliary catalyst is converted under the reaction conditions into a catalytically active carbene complex. The posttreatment is conventionally accomplished by heating in atmospheres of air, water vapor, a hydrocarbon, or an inert gas. A temperature in the range from 400° to 1000° C. has been used.

During the preparation of the catalyst in accordance with the invention, different temperatures can be applied during pretreatment, bonding of tungsten and posttreatment. A premise for the procedures is, however, that all process steps are carried out above the condensation limit temperature $T_{min}$ for each reagent.

The present invention achieves significant benefits. For instance, a low tungsten content in the catalyst results in a catalyst with an activity equal to that of a catalyst of appreciably higher tungsten content that has been prepared by the methods of the prior-art technology. Further, the distribution of the metallic species in the catalyst is more homogeneous, and the dispersion of the metal species onto the support surface is better than in catalysts prepared using liquid processes. The controllability of metal species bonding during the preparation of the catalyst is improved. Bonding of several metal species becomes easier than from the liquid phase. The metal species can be bonded on the support in different compounds, whereby suitable ligands are provided in the catalyst.

A catalyst prepared according to the invention for metathetic reactions typically has a very high stability, which makes it extremely durable under process conditions. During wear in use, its properties change in such a fashion that its metathetic activity is increased and the catalytically active acid sites that can promote side reactions are deactivated.

Support materials capable of bonding a tungsten compound in accordance with the invention are advantageously oxides of silicon or aluminum, or mixtures thereof. Cogels formed by combining silica gel with, e.g., magnesium oxide or titanium oxide can also be employed. The silica-magnesia cogel in particular is advantageous due to its reduced tendency to support side reactions catalyzed by acid sites.

The vaporizable precursors of the tungsten species are selected from compounds having sufficiently high vapor pressures at the partial vacuum levels applied. Halides of tungsten, such as tungsten oxychloride or hexachloride, or mixtures thereof, are advantageously employed according to the invention. In addition to the compounds listed above, also organotungsten compounds, such as alkyl or heterocyclic compounds of tungsten, may be employed. As mentioned above, the W species content can be controlled by a suitable choice of the reactant. Exemplifying the case, it can be noted that the saturation level remains lower for $WCl_6$ than for $WOCl_4$ when employing the same pretreatment and bonding temperature.

The invention is next examined with the help of exemplifying tests of non-limiting character. It should be noted that the unit of activity g/g·h used in the activity tests indicates the quantity of reacted propene (in grams) per quantity of tungsten (g) and time (h).

EXAMPLE 1

The catalysts were prepared using fine-grain silicon dioxide (PQ cs.1231, Grace Co., #432) as the support. The support material was placed into the reaction space and heated at 200° C. at approximately 50 mbar nitrogen pressure for 18 hours. The purpose of the heat treatment was to remove the physically absorbed water from the support and also a part of the chemically bonded water and OH groups. Next, the reaction space was heated to 220° C. Tungsten oxychloride was heated to 200° C. for evaporation and the vapor was subsequently routed in a nitrogen carrier stream into the reaction space for 3 hours, after which the catalyst was flushed with nitrogen for approx 9 hours. The reaction space temperature during the entire bonding process of the W species was 220° C.

The behaviour of the prepared catalyst was examined in the disproportionation reaction of propene to ethene and butene. The reaction is reversible ($\Delta H = 1.3$ kJ/mol) and the conversion of propene in the equilibrium is about 42%. Prior to the test, the catalyst was activated by heating in the reactor at 600° C. for 2 hours in a stream of dry air at 10 l/hours. After the air-stream calcining, the catalyst was flushed with nitrogen at 600° C. for 0.5 hours. Then, the reactor was cooled to 400° C. and the propene feed was started at two different rates: 1 l/min and 6 l/min, respectively.

The reactor space was a quartz vessel into which the 200 to 500 mg of the catalyst was loaded for each test run.

The tungsten content of the catalyst was 8.6 wt % prior to the reaction and 7.7 wt % after the reaction. The chlorine content of the catalyst was 3.7 wt % prior to the reaction. The activity of the catalyst was 21.95 g/g·h at 1 l/h flow rate and 120.35 g/g·h at 6 l/h flow rate.

EXAMPLES 2 TO 11

Tungsten-containing catalysts were prepared according to example 1 from $WOCl_4$ and $WCl_6$, respectively, and their catalytic activity was determined in the manner described above. The silica support of the $WCl_6$ catalyst was #432 by Grace Co.

An outline of the results is given in Table 1 below.

Reference Example

A reference catalyst was prepared by impregnating a silica support twice with a 4% ammonium tungstenate solution with an intermediate drying of the support free from water in an oven heated to 115° C. The W species content of the prepared catalyst was 2.3 wt %.

The catalyst was activated as above and its activity was examined as described in Example 1. The results are given in Table 1.

Examination of the Results

As is evident from the results of Table 1, the surface-site selective method according to the present invention can be employed for preparing catalyst having an activity at least as good as those made using conventional impregnation techniques.

FIG. 1 illustrates the same results in graphic form, whereby the catalysts according to the present invention have an activity which is up to 5 times higher at the same metal species content.

Figure 2:
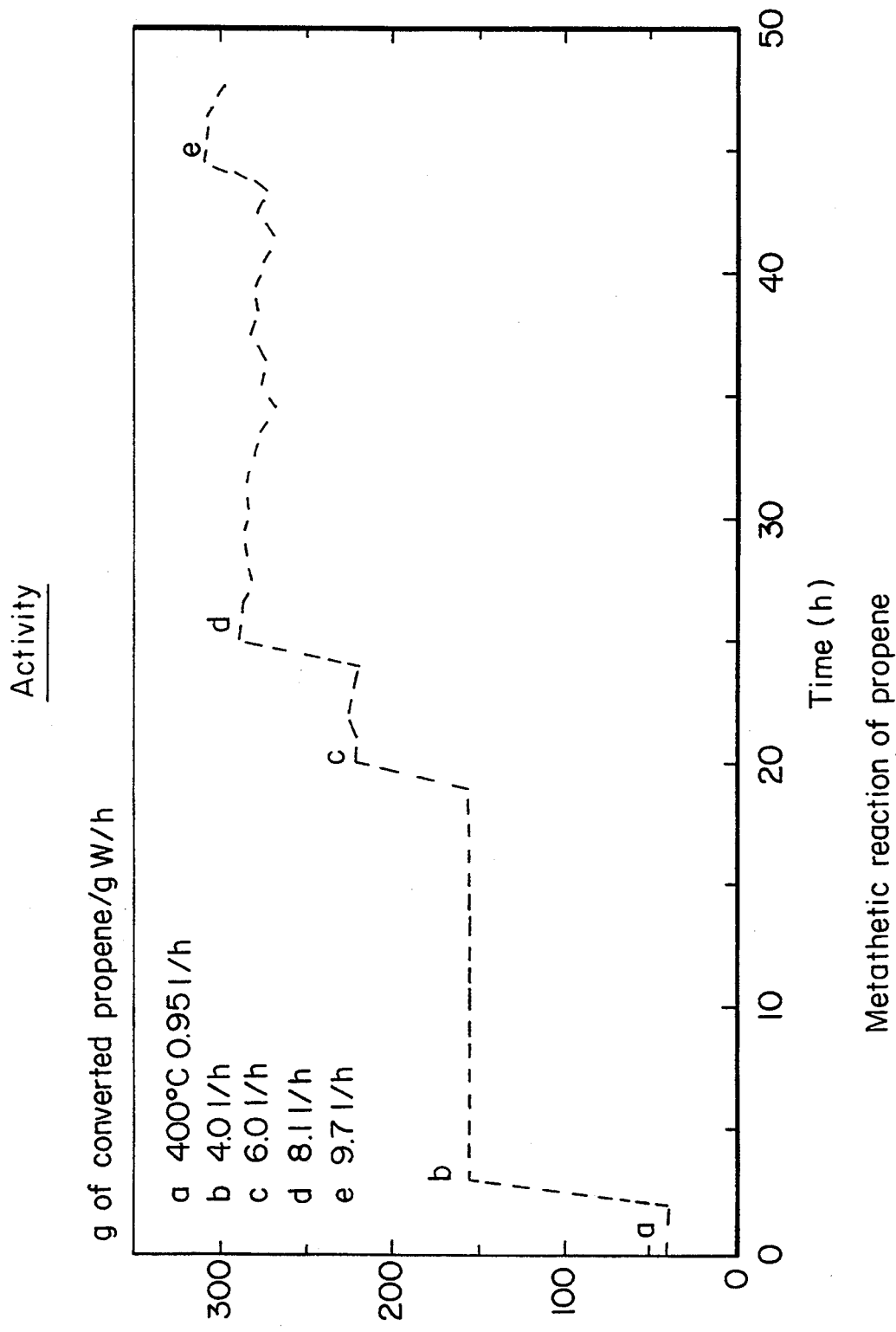
FIG. 2 is a graph showing the activity of one of the catalysts in a corresponding reaction as a function of time for different feed rates of propene.

FIG. 2 illustrates further the catalyst activity measured in the test #11 in a metathetic reaction of propene as a function of time and the feed rate of propene. The reaction temperature is kept constant at 400° C. As can be seen from the diagram, the catalyst activity increases from a level of 40 g propene/g W/h at 0.95 l/h feed rate to 300 g propene/g W/h at 9.7 l/h feed rate.

TABLE 1

Catalyst preparation conditions and activities in a metathetic reaction of propene

| Test run no. | Pre-treatment T[°C.] | Pre-treatment t[h] | Oven treatment (8 h) T[°C.] | Evaporation temp. T[°C.] | Run temp. T[°C.] | Total reaction and nitrogen flush time [h] | Calcining** Gas stream | Calcining** Temp. T[°C.] | Calcining** Time t[h] | Reaction temp. T[°C.] |
|---|---|---|---|---|---|---|---|---|---|---|
| Using $WOCl_4$ as the precursor of the tungsten species | | | | | | | | | | |
| 1 | 200 | 18 | — | 200 | 220 | 12 | air | 600 | 2 | 400 |
| 2 | 200 | 3 | 200 | 200 | 420 | 8 | air | 600 | 2 | 400 |

TABLE 1-continued

Catalyst preparation conditions and activities in a metathetic reaction of propene

| | | | | | | | | | | | |
|---|---|---|---|---|---|---|---|---|---|---|---|
| 3 | 200 | 3 | 200 | 200 | 220 | 8 | air | 600 | 2 | 400 | |
| 4 | — | — | — | — | — | — | prop. | 400 | 0.5 | 400 | |
| 5 | 400 | 3 | 400 | 200 | 220 | 12 | air | 600 | 2 | 400 | |
| 6 | 400 | 3 | 400 | 200 | 320 | 8 | air | 600 | 2 | 400 | |
| 7 | — | — | — | — | — | — | $N_2$ | 600 | 2.5 | 400 | |
| 8 | 400 | 3 | 400 | 200 | 420 | 8 | air | 600 | 2 | 400 | |
| Using $WCl_6$ as the precursor of the tungsten species | | | | | | | | | | | |
| 9 | 400 | 3 | 400 | 240 | 400 | 1 | air | 600 | 2 | 400 | |
| 10 | 400 | 3 | 400 | 240 | 330 | 1 | air | 600 | 2 | 400 | |
| 11 | 330 | 3 | 330 | 160 | 330 | 2.5 | air | 600 | 2 | 400 | |
| Reference catalyst prepared by Impregnation | | | | | | | air | 600 | 2 | 400 | |

| Test run no. | Fresh catalyst W cont. [%] | Fresh catalyst Cl cont. [%] | Cl/W | Used catalyst W cont. [%] | Used catalyst Cl cont. [%] | Activity at nitrogen flow of 1 l/h [g/g.h] | Activity at nitrogen flow of 6 l/h [g/g.h] |
|---|---|---|---|---|---|---|---|
| Using $WOCl_4$ as the precursor of the tungsten species | | | | | | | |
| 1 | 8.6 | 3.7 | 0.43 | 7.7 | — | 21.95 | 120.35 |
| 2 | 6.1 | 3.3 | 0.54 | — | — | 43.17 | 218.19 |
| 3 | 9.5 | 3.0 | 0.32 | 8.9 | — | 30.10 | 149.44 |
| 4 | — | — | — | — | — | 28.21 | 140.11 |
| 5 | 5.4 | 3.3 | 0.61 | — | — | 57.89 | 266.26 |
| 6 | 5.6 | 2.8 | 0.50 | 5.8 | — | 32.64 | 124.28 |
| 7 | — | — | — | — | — | 34.00 | — |
| 8 | 5.2 | 3.1 | 0.60 | — | 0.82 | 39.22 | 184.05 |
| Using $WCl_6$ as the precursor of the tungsten species | | | | | | | |
| 9 | 2.6 | 3.1 | 1.19 | — | — | 92.14 | 413.47 |
| 10 | 3.5 | 5.4 | 1.54 | — | — | 80.69 | 324.53 |
| 11 | 4.5 | 6.0 | 1.33 | — | — | 39.69 | 221.72 |
| Reference catalyst prepared by Impregnation | | | | | | | |
| | 2.3 | 0.44 | 0.19 | 2.2 | — | 34.13 | 80.91 |

**After calcining in air, the catalysts were flushed with $N_2$ at 600° C. for 0.5 h except the propene-calcined catalyst no. 4.

EXAMPLE 12

Figure 3:
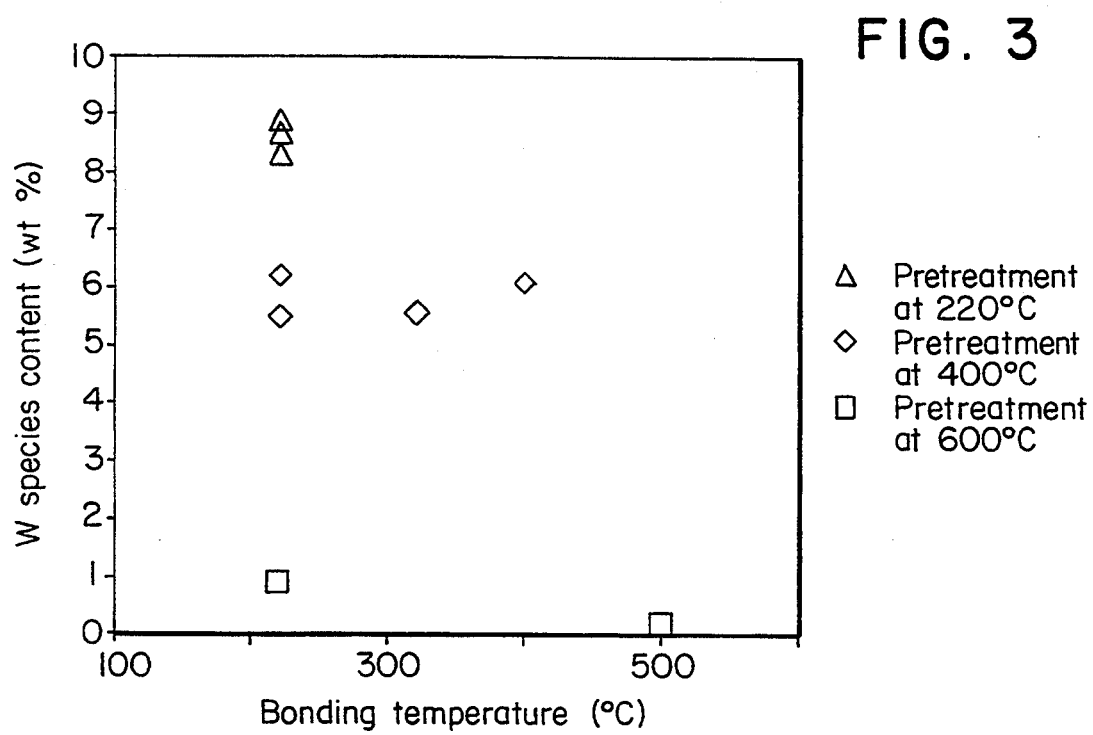
FIG. 3 is a graph showing the effect of the pretreatment and bonding temperatures on the tungsten species content of the catalyst when $WOCl_4$ is used as the precursor.

Investigations of the effect of the pretreatment temperature, reagent and support on the tungsten content The effect of the preheating and bonding temperatures on the tungsten content were examined by preparing several catalyst samples in the same fashion as in Example 1 using tungsten oxychloride as the reagent for the tungsten species and a silica support (320 m²/g). Prior to the bonding reaction, the support was treated at 220° C., 400° C. and 600° C., respectively, overnight in an air atmosphere. The pretreatment was continued in a reactor for 3 hours. The bonding reaction was carried out at 220° C., 330° C., 360° C. and 500° C., respectively. The tungsten content of the produced W/SiO₂ catalysts are shown in FIG. 3 as a function of the bonding temperature for the different pretreatment temperatures. As can be seen from the results, an appreciably higher amount of tungsten can be bonded to the support at a lower pretreatment temperature (220° C.) than at a higher temperature (600° C.). By contrast, the bonding temperature has no significant effect on the tungsten content.

The above-described tests were also performed using tungsten hexachloride replacing the tungsten oxychloride, whereby a similar temperature dependence of the tungsten bonding was found. The tungsten contents obtained using $WCl_6$ were, however, throughout lower than those obtained using $WOCl_4$.

Finally, comparative tests were carried out using alumina instead of silica gel as the support for bonding the tungsten oxychloride and hexachloride. The results are shown in Table 2.

TABLE 2

Bonding $WOCl_4$ and $WCl_6$ on alumina and silica gel supports.

| Support | Reagent | W/atoms per nm² |
|---|---|---|
| $Al_2O_3$ | $WOCl_4$ | 0.44 |
| | $WCl_6$ | 0.26 |
| $Si_2$ | $WOCl_4$ | 0.63 |
| | $WCl_6$ | 0.34 |

On the basis of the above-shown test results it is obvious that the tungsten content of the catalysts being prepared can be appropriately controlled by varying the pretreatment temperature, the reactant and the support, and to some extent, the bonding temperature.

EXAMPLE 13

Catalysts were prepared under the conditions applied in Example 1 using tungsten oxychloride as the reagent and a cogel of silica and magnesia as the support in which the magnesium oxide content was approximately 0.1 wt %.

The catalysts were calcined in air and flushed with nitrogen (600° C., 2 hours) and their activities were measured in the conversion reaction of propene to ethene and butene at 400° C.

The test results are shown in Table 3.

TABLE 3

Activities of $WO_3$ catalysts on cogel of silica-magnesia support for different flow rates (WHSV)

| Support | Mg [%] | W [nm⁻²] | TOF [$s^{-1}$] 4 $h^{-1}$ | TOF [$s^{-1}$] 25 $h^{-1}$ | TOF [$s^{-1}$] 86 $h^{-1}$ |
|---|---|---|---|---|---|
| $SiO_2$—MgO | 0.1 | 0.37 | 0.041 | 0.11 | 0.33 |

TABLE 3-continued

Activities of WO₃ catalysts on cogel of silica-magnesia support for different flow rates (WHSV)

| Support | Mg [%] | W [nm⁻²] | TOF [s⁻¹] 4 h⁻¹ | 25 h⁻¹ | 86 h⁻¹ |
|---------|--------|----------|-----------------|--------|--------|
| cogel   | 0.1    | 1.70     | —               | —      | 0.32   |

TOF: Turnover frequency
WHSV Propene flow rate through the catalyst relative to one gram (1 g) of the catalyst
TOF Number of reacted propene molecules per one tungsten atom in one second As mentioned in the introductory part of the above description, the use of a cogel provides the specific advantage of diminishing the rate of side reactions catalyzed at the acid sites.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A heterogeneous catalyst for liquid- or vapor-phase metathetic reactions of olefins, comprising catalytically active species of tungsten on an inorganic support, said catalyst having been prepared by
   vaporizing a tungsten-containing reagent selected from the group consisting of tungsten oxychloride and tungsten hexachloride,
   routing the vapor of the tungsten-containing reagent into a reaction space where the vapor is reacted with the support material at about 160° to about 500° C.,
   maintaining the vapor pressure of said tungsten-containing reagent sufficiently high and the duration of interaction with said support material sufficiently long so as to provide said reagent in an amount at least equal to the number of available bonding sites of said support material, and
   removing said tungsten-containing reagent not bonded to said support material from the reaction space in the vapor phase.

2. The catalyst as claimed in claim 1, wherein said tungsten-containing reagent is tungsten oxychloride.

3. The catalyst as claimed in claim 2, wherein said tungsten oxychloride is vaporized at about 200° C. and is reacted with said support at about 220° to 420° C.

4. The catalyst as claimed in claim 1, wherein said tungsten-containing reagent is tungsten hexachloride.

5. The catalyst as claimed in claim 4, Wherein said tungsten hexachloride is vaporized at about 160° to 240° C. and is reacted with the support at about 330° to 400° C.

6. The catalyst as claimed in claim 1, wherein said tungsten-containing reagent is reacted with said support at 0.1 to 100 mbar pressure.

7. The catalyst as claimed in claim 1, wherein said support is preheated for 1 to 40 hours at 200° to 600° C. prior to reacting said vaporized tungsten-containing reagent with said support.

8. The catalyst as claimed in claim 1, wherein the reaction time between said tungsten-containing reagent and said support material is 0.5 to 25 hours.

9. The catalyst as claimed in claim 1, wherein said preparation further comprises a post treatment step, which comprises heating said catalyst in the presence of air, water vapor, a hydrocarbon or an inert gas.

10. The catalyst as claimed in claim 1, wherein said support is silica gel or a cogel of silica gel and magnesium oxide.

11. The catalyst as claimed in claim 7, wherein said support is preheated for 2 to 24 hours.

12. A heterogeneous catalyst, comprising catalytically active species of tungsten on an inorganic support, wherein said catalyst is prepared by combining a vaporous tungsten-containing reagent with an inorganic support at a temperature of about 160° C. to about 500° C. and under a vapor pressure that is sufficiently high and a duration that is sufficiently long so that the amount of said reagent provided is at least equal to the number of available bonding sites on said inorganic support and thereby chemically bonding said vaporous reagent to said support.

* * * * *